United States Patent [19]

Clark, Jr.

[11] Patent Number: 4,490,351
[45] Date of Patent: Dec. 25, 1984

[54] METHODS OF TREATING DISORDERS OF AN EYE WITH LIQUID PERFLUOROCARBONS

[75] Inventor: Leland C. Clark, Jr., Cincinnati, Ohio

[73] Assignee: Children's Hospital Medical Center, Cincinnati, Ohio

[21] Appl. No.: 358,055

[22] Filed: Mar. 15, 1982

[51] Int. Cl.$^3$ .................... A61K 49/04; A61K 31/025
[52] U.S. Cl. ......................................... 424/5; 424/352
[58] Field of Search .................................. 424/5, 352

[56] References Cited

U.S. PATENT DOCUMENTS

| 3,911,138 | 10/1975 | Clark, Jr. | 424/252 |
| 4,105,798 | 8/1978 | Moore et al. | 424/252 |
| 4,141,973 | 2/1979 | Balazs | 424/180 |
| 4,285,928 | 8/1981 | Wada et al. | 424/5 |

OTHER PUBLICATIONS

Gholam A. Peyman, M.D., et al., "A Review of Substances and Techniques of Vitreous Replacement", *Survey of Ophthalmology,* vol. 17, No. 1, 1972, pp. 41-51.
Stone, William, Jr., M.D. "Alloplasty in Surgery of the Eye" *The New England Journal of Medicine,* vol. 258, No. 10, 1958, pp. 486-490.
Gloor, Balder P., M.D., "The Vitreous", *Adler's Physiology of the Eye Clinical Application,* 7th Ed., 1981, pp. 255-276.
Swann, David A., "I. The Preparation and Properties of Rooster Comb Hyaluronic Acid", *Biochimica et Biophysica Acta,* 156, 1968, pp. 17-30.
Vygantas, Charles M., M.D., et al., "Octafluorocyclobutane and Other Gases for Vitreous Replacement", *Arch. Ophthalmol.,* vol. 90, Sep. 1973, pp. 235-236.
Lincoff, Harvey, M.D., et al., "Intravitreal Longevity of Three Perfluorocarbon Gases", *Arch. Ophthalmol.,* vol. 98, Sep. 1980, pp. 1610-1611.
Vygantas, Charles M., "Octafluorocyclobutane ($C_4F_8$) Gas as Vitreous Replacement", *Vitreous Surgery and Advances in Fundus Diagnosis and Treatment,* 1977, pp. 423-425.

*Primary Examiner*—Frederick E. Waddell
*Attorney, Agent, or Firm*—Wood, Herron & Evans

[57] ABSTRACT

Liquid perfluorocarbons and substituted derivatives thereof are used as fluid substitutes for the vitreous or the aqueous of the eye. These liquids are also used to transparentize the cornea or lens when either becomes opacifed due to degeneration or cataract formation. Methods involving the use of these liquids during retinal surgery or diagnostic procedures of the eye are also disclosed.

30 Claims, 1 Drawing Figure

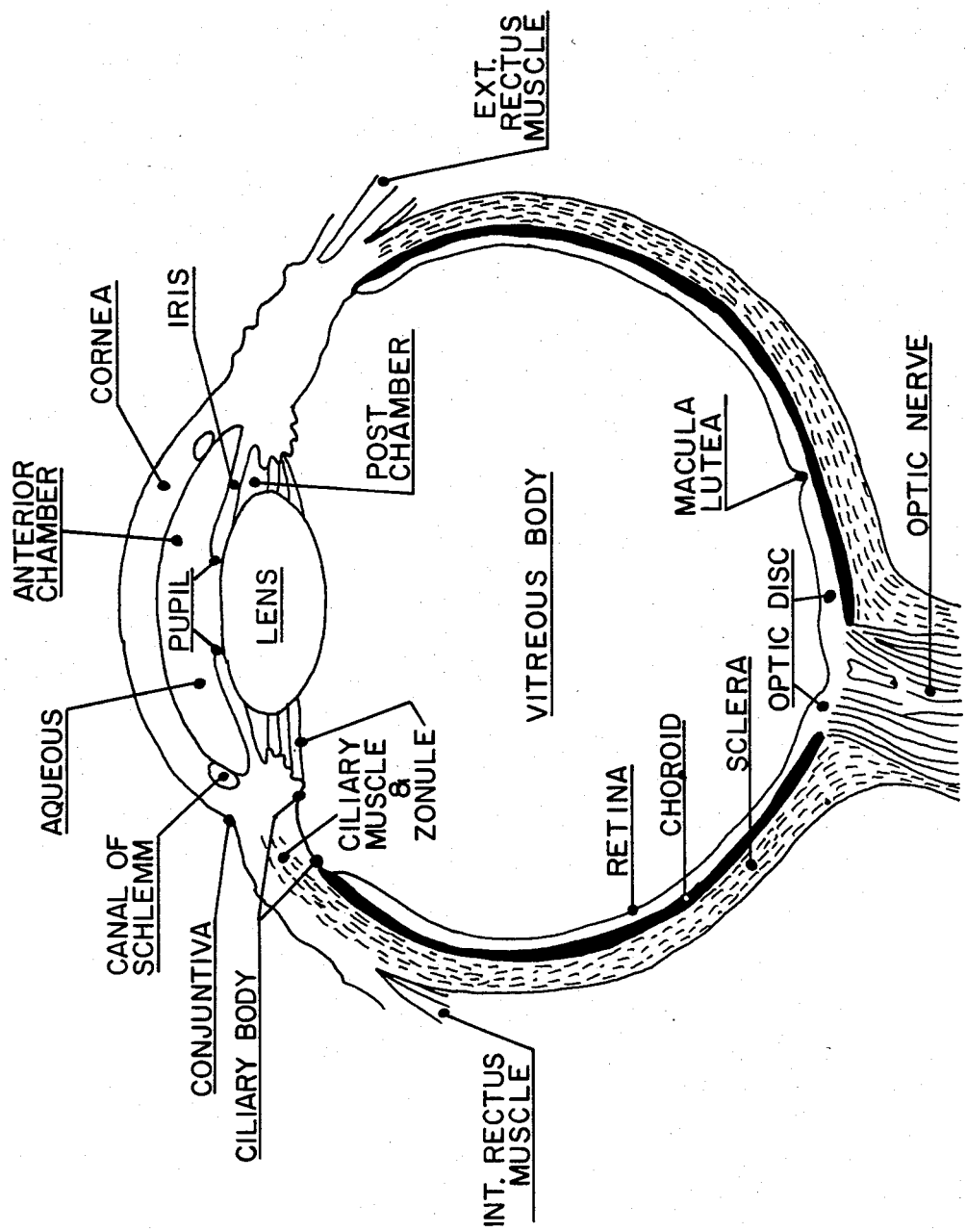

METHODS OF TREATING DISORDERS OF AN EYE WITH LIQUID PERFLUOROCARBONS

BACKGROUND OF THE INVENTION

The eye, which is responsible for vision, is probably the most remarkable organ in animals. It is comprised of many complex components, for example, cornea, aqueous humor, lens, vitreous and retina, with each having its own highly specialized function contributing significantly to the overall visual experience. Unfortunately, each section of the eye is susceptible to well-known pathological disorders which can reduce the quality of vision and/or resulting in partial or total blindness. Such pathological processes comprise vitreous liquefaction and opacification, retinal detachment, glaucoma, and opacification of the lens and cornea.

The vitreous is a remotely oxygenated transparent mass that in most animals is physically a gel-like substance. It consists predominantly of water and fills the posterior chamber of the eye. The vitreous functions to give shape to the eye, transmit light, and form a semi-solid support for the retina against the choroid. When the vitreous is physically altered or becomes opaque, permanent blindness can develop. For example, should the vitreous partially liquify, as it often does with age, its supporting capability is diminished and retinal detachment may result. It is well appreciated that retinal detachment is the leading cause of blindness in the United States.

Furthermore, the vitreous may become opaque as a direct consequence of cellular infiltration or hemorrhage. Cellular infiltrations are common in a number of inflammatory processes of tissue surrounding the vitreous. As a result of inflammation, opacification degeneration of the vitreous may be seen. Vitreous hemorrhage is also very common, particularly in diabetics, and occurs when the retina ciliary body ruptures and hemorrhages into the vitreous developing large opaque areas. Unlike most other tissue, however, the vitreous is avascular and does not contain significant macrophages. Therefore, if foreign agents or blood penetrate into the vitreous, they may permanently remain in the vitreous thereby leading to partial or total vision impairment. In either disease process, liquefaction or opacification of the gel-like substance, vitreous replacement with a suitable substitute is required.

For several years, surgical removal and replacement of the vitreous with a less than optimal substitute has been known. Vitreous replacement has been accomplished by a variety of liquids including salt solutions, vitreous humor from animals, spinal fluids and other substances thought to have desirable properties. *Survey of Ophthalmology:* "A Review Of Substances And Techniques Of Vitreous Replacement" by G. H. Peyman, E. S. Ericson and D. R. 17:41-51, May, 1972. Silicone oils (dimethylsiloxanes of various viscosities) have been used for partial replacement of vitreous humor with success but have doubtful application because of pathological changes after long term replacement. *New England Journal of Medicine:* "Alloplasty In Surgery Of The Eye" by W. Stone, Jr., 258:486-490, 1958. There also have been reported results from the use of lyophilized vitreous, pure hyaluronic acid, or polygeline and the use of collagen is still in its experimental stage. Gloor, B.P.M.P.IN: Moses R. A. (Pd.) *alters physiology of the eye.* Clinical application. 7th Ed. St. Louis: C. V. Mosby Company, p. 270 (1971). *Biochimica et Biophysica Acta:* "Studies On Hyaluronic Acid". The Preparation And Properties Of Rooster Comb Hyaluronic Acid" by D. A. Swann, 156: 17-30 (1968) and U.S. Pat. No. 4,141,973, issued Feb. 27, 1979 to Balazs.

Out of the presently available vitreous replacements, salt solutions, silicone oils and hyaluronic acids are predominantly used even though they are less than optimal substitutes with each having its own major disadvantages. Salt solutions are not readily compatible with the retina or the optic nerve, yielding some disintegration of vision, changes at the end of the optic nerve and retinal unhealthiness. Silicone oils, in addition to their toxicities, also tend to emulsify and break-off into droplets, a process often called "fish-egging", thereby enhancing their turbidity. Finally, hyaluronic acid is very expensive, difficult to produce and has a fixed viscosity. Since hyaluronic acid is derived from rooster combs, its supply is limited.

Most knowledge of present vitreous replacement concerns the uses of gases such as air, nitrogen, and sulfurhexafluoride. The first fluorocarbon to be used as a gas in the vitreous was octafluorocyclobutane or perfluorocyclobutane. *Archives of Ophthamology:* "Octafluorocyclobutane And Other Gases For Vitreous Replacement" by C. M. Vygantas, G. A. Peyman, M. J. Daily and E. S. Ericson 90:235-236, 1973. Other perfluorocarbon gases more recently tested are perfluoromethane, perfluoroethane and perfluoropropane. *Archives of Ophthamology:* "Intravitreal Longevity Of Three Perfluorocarbon Gases" by H. Lincoff, J. Mardirossian, A. Lincoff, P. Ligett, T. Iwamoto and F. Jakobjec, p. 1610, 1980. Perfluoro-n-butane and perfluoroisobutane have also been studied. *Vitreous Surgery And Advances In Fundus Diagnosis And Treatment,* "Octafluorocyclobutane ($C_4F_8$) Gas As Vitreous Replacement" by C. M. Vygantas pp. 423-425, 1975. These gases are being used because they are biologically inert, insoluble in water and pass through membranes very slowly. They, therefore, equilibrate with blood gases ($O_2$, $CO_2$, $N_2$) in the vitreous and reach an equilibrium condition after hours or days. The equilibrium finally reached is a function of the partial pressure of the particular gas as well as the blood gases. However, since perfluorocarbon gases are compressible, they will remain in an equilibrium state only as long as the gas pressure is essentially unchanged. For example, the gases would increase in volume during an airplane flight while their volume would probably also change during anesthesia because most anesthetic gases rapidly diffuse through body tissues. Fluorinated anesthetics might represent particularly complicated gas-vapor level equilibrium. Because of these undesired properties, among others, perfluorocarbon gases are less than optimal as vitreous replacements. However, in spite of considerable work reported in connection with vitreous replacement, as set forth herein above, there is no ideal gelatinous substitute for the complex glycoprotein structure of the vitreous body. Known vitreous replacements are not completely satisfactory because they may cause post-operative complications resulting in total blindness. Vitreous substitutes, thus, have somewhat fallen into disrepute because basic researchers have had difficulty introducing a substitute that is clear, inert, well tolerated, and remains viscous long enough.

The retina comprises the innermost tunic of the eyeball containing the nervous elements for reception of visual stimulae. The phenomenon of detachment of the retina consists of physical separation of the retina from its juxtaposition to the choroid. The most important factor contributing to retinal detachment is liquefaction and shrinkage of the vitreous, commonly known as vitreous retraction. In addition, vitreous retraction generated by vitreous shrinkage may produce retinal tear with or without retinal detachment. There are presently three methods of treatment for retinal tear with or without retinal detachment. The first consists of scleral buckling (forcing the anterior wall of the choroid against the posterior side of the retina) which utilizes an external encircling band in retinal tears and detachments. Also, removal of the entire vitreous gel from the vitreous cavity may be utilized in retinal detachment. However, this procedure is utilized only in extreme cases. The third method requires the patient to lie on his ventral surface while the physician introduces into the posterior chamber an air bubble (having a specific gravity less than vitreous fluid) in order to force the detached retina back against the choroid. Moreover, the patient must remain on his ventral surface during the early recovery stage, perhaps for many days. All three forms of treatment appear to be quite inconvenient to the patient as well as to the physician, and constitute somewhat extreme methods of treatment.

The aqueous humor is the fluid produced in the eye which fills the anterior chamber, located between the cornea and the lens. Because aqueous humor is being produced constantly, its rate of formation and exit from the eye is directly related to the steady straight level of intraocular pressure. In "glaucoma", elevated intraocular pressure is related to the eye's reduced capability to facilitate outflow of aqueous humor. Thus, the abnormally high pressure squeezes against the retina, occluding circulation in the choroid and retina, the optic disk becomes distorted and concave, and blindness results. The primary treatment for glaucoma presently is to medicate the eye with a drug that decreases the rate of aqueous humor formation. The present course of therapy is to suppress the rate at which aqueous humor is formed. But it appears possible to totally replace the aqueous humor in glaucoma. The problem with replacing aqueous humor, however, is to find a suitable substance. Heretofore, there have been no attempts to replace the aqueous humor with substitutes.

The cornea and lens are normally transparent to provide refracting surfaces for the optical system of the eye. Any change in the transparency of the cornea or the lens will seriously interfere with the clarity of the retinal image. Nevertheless, the cornea and lens are subject to loss of transparency and will develop opacity depending upon the disease process as to which each may be affected. Presently, the opaque areas in the cornea and lens are surgically removed. In addition, the lens is often totally removed, for example in cataract surgery. The undesirable complications that can develop from surgical treatment of opaque areas within the cornea and lens are well known. Moreover, if surgical removal of the opaque areas is successful, vision will probably remain impaired and even possibly incorrectable.

It is apparent from the above brief overview of various disorders of the eye and the current state of knowledge that there are critical needs which must be met, and problems to be solved, so that the precious phenomenon of eyesight may be either restored or preserved.

SUMMARY OF THE INVENTION

Liquid perfluorocarbons and substituted derivatives thereof have been found to be substitutes for the vitreous or aqueous. Also, such liquids can be forced into opaque areas within the cornea or lens and transparentize them so that vision may be restored. These liquids can be introduced into the vitreous to treat retinal tears (rips) or detachments. Other radiopaque liquids can be introduced into the eye for diagnostic purposes.

This invention is directed to the use of perfluorocarbon liquids and substituted derivatives thereof in ophthalmological disorders. Perfluorocarbons have been found to be advantageous substitutes for the liquids within the eye as well as transparentizing agents for the cornea and lens. These liquids have been introduced into eyes of experimental animals to function as vitreous and aqueous humor substitutes, and as transparentizing agents. They have been proven to be useful substitutes, and experimental animals treated with these liquids not only maintain normal vision, but can live normal lives after treatment. Furthermore, the perfluorocarbons surprisingly are retained indefinitely within the eye, particularly within the cornea and lens, as well as the posterior and anterior chambers. These and other remarkable discoveries will become further understood in the details which follow.

The perfluorocarbon liquids are preferably transparent or light transmissive, inert, remain viscous indefinitely, and can be chemically designed to have certain viscous and elastic properties. Moreover, neat fluorocarbon liquids generally dissolve at least 20 times as much oxygen and carbon dioxide as water, aqueous or vitreous, have zero oncotic pressure (like vitreous), are more dense than water, are immiscible with blood or water, and can be sterilized by autoclaving. Thus, these liquids are comprised of unusual chemical and physical properties endowing them with unique, unexpected and advantageous uses in ophthalmological disorders. Exemplary of suitable perfluorocarbon liquids and substituted derivatives are perfluorooctylbromide (PFOB), perfluoro 1-methyldecalin (PP9), and perfluoro 1, 3-dimethyladamantane and perfluorotrimethylbicyclo[3.3.1.]nonane mixtures (DAWN).

Thus, this invention is predicated in part upon the discovery that perfluorocarbon liquids are ideal as substitutes for the vitreous and aqueous humor. They are inert, transparent or light transmissive, and well tolerated. As such, they fulfill outstanding needs in eye disorders such as replacement of cloudy or opaque vitreous after hemorrhages and inflammatory processes. Another important discovery involved in this invention is that these liquid perfluorocarbons can be introduced into opaque areas within the cornea or lens providing transparent "windows" therein to enhance an otherwise obstructed visual process. Remarkably, these windows are fairly permanent and localized in the tissue.

Furthermore, these dense compounds, having specific gravities greater than one, can be ideally employed in the treatment of retinal tears or detachments. For instance, currently a physician, during surgery or treatment of a patient during retinal detachment, will lie on his back and the patient is lying on his posterior surface. In contrast, the use of liquids of this invention during such treatment enables the detached retina to be mechanically supported against the choroid while the patient rests on his back and the physician stands or sits in a normal position. The novel liquids may simply be removed after the retina is attached, if desired.

In another aspect of this invention, substituted perfluorocarbon liquids, e.g., PFOB, can be introduced into the eyes as radiopaque agents to X-ray intraocular structures. Such diagnostic techniques are very much needed, especially as here where inert liquids may be employed.

DETAILED DESCRIPTION OF THE INVENTION

The perfluorocarbons and any derivatives thereof may be generally termed as "liquids". The term "liquids", as used herein, is a comprehensive designation incorporating compounds that are in a state neither solid or gaseous such as liquids, emulsions and gels. The term "perfluorocarbon" means a "cyclic" or "acyclic" compound of carbon. Whereas the term "substituted derivatives thereof" characterizes substituted perfluorocarbons with chemical elements within their structures such as oxygen, nitrogen and bromine, etc. It should also be noted that the term "perfluorocarbon" denotes substitution of all hydrogen atoms attached to the carbon atom chain or ring and any carbon side groups with fluorine. It is conceivable in the manufacture of such compounds that minor amounts of substantially fluorinated derivatives may be mixed with completely fluorinated compounds. This is permissible providing that the lack of complete replacement of all hydrogens does not affect the essential characteristics of the liquid perfluorocarbons of this invention, particularly when active hydrogens critically enhance the toxicity of the compounds. Among the perfluorocarbon compounds which may be employed are perfluorotributylamine (FC47), perfluorodecalin (PP5), perfluorotetrahydrofuran (FC80), perfluoroether (PID) [(CF$_3$)$_2$CFOCF$_2$(CF$_2$)$_2$CF$_2$OCF(CF$_3$)$_2$], perfluoroether (PIID) [(CF$_3$)$_2$CFOCF$_2$(CF$_2$)$_6$CF$_2$OCF(CF$_3$)$_2$],

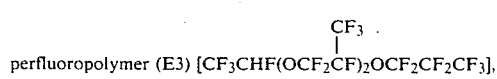
perfluoropolymer (E3) [CF$_3$CHF(OCF$_2$CF)$_2$OCF$_2$CF$_2$CF$_3$],

perfluoropolymer (E4) [CF$_3$CHF(OCF$_2$CF)$_3$OCF$_2$CF$_2$CF$_3$], perfluoroetherpolymer (Fomblin Y/01), perfluorododecane, perfluorobicyclo[4.3.0]nonane, perfluorotrimethylcyclohexane, perfluoroisopropylcyclohexane, perfluoroendotetrahydrodicyclopentadiene, perfluoroadamantane, perfluoroexo-tetrahydrodicyclopentadiene, perfluorobicyclo[5.3.0.]decane, perfluorotetramethylcyclohexane, perfluoro-1-methyl-4-isopropylcyclohexane, perfluro-n-butylcyclohexane, perfluorodimethylbicyclo[3.3.1.]nonane, perfluoro-1-methyl adamantane, perfluoro-1-methyl-4-t-butylcyclohexane, perfluorodecahydroacenaphthene, perfluorotrimethylbicyclo[3.3.1]nonane, perfluoro-n-undecane, perfluorotetradecahydrophenanthrene, perfluoro-1,3,5,7-tetramethyladamantane, perfluorododecahydrofluorene, perfluoro-1,3-dimethyl adamantane, perfluoro-n-octylcyclohexane, perfluoro-7-methyl bicyclo[4.3.0.]nonane, perfluoro-p-diisopropylcyclohexane, and perfluoro-m-diisopropylcyclohexane.

It is to be understood that perfluorocarbon liquids of this invention may be formed of "neat" perfluorocarbon liquids; emulsions, suspensions or solutions of perfluorocarbons in mixture with themselves or other solvents. For instance, perfluoro-1,3-dimethyl adamantane is normally a solid but in mixture with perfluorotrimethylbicyclo[3.3.1.]nonane a liquid is formed, i.e., DAWN. Also, when the perfluorocarbon liquids are emulsified in water, sometimes milky or even somewhat clear or transparent liquids, emulsions, gels or solutions might result which may be suitable for use in this invention. Of course, ideally for vitreous substitutes transparency is preferred. On the other hand, some eyesight is better than none, therefore, even somewhat milky fluids may be used. Where the liquids are used in surgery for retinal repair, the property of transparency is not important. In brief, then, the nature of the "liquid" state may include pure liquid perfluorocarbon, emulsions, solutions, suspensions, etc., of perfluorocarbon compounds in other liquid mediums. Incorporated herein by reference, therefore, are emulsions or suspensions of perfluorocarbons disclosed in U.S. Pat. Nos. 3,911,138 and 4,105,798 as suitable liquids for use in this invention. The following TABLE I lists certain presently preferred perfluorocarbon liquids.

TABLE I

| TRADE NAMES | CHEMICAL NAMES | EMPIRICAL FORMULA | MOLECULAR WEIGHT | BOILING POINT | VAPOR PRESSURE torr | SPECIFIC GRAVITY | REFRACTIVE INDEX |
|---|---|---|---|---|---|---|---|
| PP9 | perfluoro(1-methyl-decalin | C$_{11}$F$_{20}$ | 512 | 160° C. | 5.2 (37.5° C.) | 1.9720 | 1.299 at 23° C. |
| PFOB | perfluorooctylbromide | C$_8$F$_{17}$Br | 499 | — | — | — | — |
| DAWN | perfluoro(1,3-dimethyl adamantane | C$_{12}$F$_{20}$ | 524 | 176° C. | 2.7 (37.0° C.) | — | 1.334 at 20° C. |
|  | perfluorotrimethyl-bicyclo[3.3.1]nonane | C$_{12}$F$_{22}$ | 562 | 177° C. | 2.5 (37.0° C.) | 2.0250 | 1.3338 at 20° C. |

In addition, other presently preferred liquid perfluorocarbons are perfluorotributylamine (FC47), perfluorotetrahydrofuran (FC80), perfluoroether (PID), Perfluoroether (PIID), perfluoropolymer (E3), perfluoropolymer (E4), perfluoroetherpolymer (Fomblin Y/01) and perfluorododecane.

The above perfluorocarbons are capable of being synthesized by either well known chemical or electrochemical processes. The chemical processes yield fairly pure substances of known structure, having well define boiling points. Whereas the electrochemical processes tend to yield a mixture of isomers, the liquids have well defined boiling points. With respect to gas chromatography, each liquid is capable of being well defined by either the packed or capillary column procedure. The standard to define each compound in gas chromatography is prepared as follows: 2 microliters of neat liquid are added to 120 milliliters of air in a sealed bottle and allowed to vaporize producing a stock standard; upon vaporization, 120 microliters of the vapor from the stock standard are added to another 120 milliliters of air in a sealed bottle producing the working standard; the sample measured by the procedure is withdrawn from the working standard, thus, a typical sample will contain 16.7 pico liters of perfluorocarbon per milliliter of standard; however, in the capillary column procedure, the sample is split into a ratio of 23:1, therefore, only 1/23 of the sample is actually measured. As indicated in Table II, the retention time is highly definitive of each liquid used in this invention. Moreover, the capillary procedure is more specific than the packed column procedure by defining additional characteristic peaks of each compound. Thus, a more precise definition of compounds can be had with the capillary column procedure.

bons", especially perfluoro (methylcyclohexane), perfluoro (1,3-dimethylcyclohexane), perfluoro (decahydronaphthalene), perfluoro (decahydro-1-methylnaphthalene) and perfluoro (decahydrodimethylnaphthalene), or mixtures thereof, perfluorinated bicyclononane, perfluorinated bicyclooctane, perfluorinated adamantane hydrocarbon, perfluoromethyladamantane and perfluorodimethylbicyclo[3.3.1.]nonane, perfluorodimethyladamantane and perfluorotrimethylbicyclo[3.3.1.]nonane, perfluorotetrahydrodicyclopentadiene and perfluorobicyclo[5.3.0.]decane, perfluorotetrahydrodicyclopentadiene, perfluorinated bicyclono-

TABLE II

| | Gas Chromatography* | |
|---|---|---|
| | Packed Column** | Capillary Column*** |
| Set up | | |
| Standard | [16.7 pl/ml]**** | [16.7 pl/ml]**** |
| Recorder Sensitivity | 0.001y full scale | 0.001v full scale |
| Column Temperature | 100° C. | 37° C. |
| Detector Temperature | 250° C. | 250° C. |
| Injector Temperature | 150° C. | 150° C. |
| $N_2$ Gas Flow | 40 ml/min | 40 ml/min |
| Split | — | 23:1 |
| Recorder Speed | 2.5 cm/min | 2.5 cm/min |
| Compounds | | |
| (1) PFOB (perfluorooctylbromide) | | |
| Attenuation | 16 | 32 |
| Sample | 10 mcl | 100 mcl |
| Peaks | 1 | 2 |
| Retention Time | | |
| $Peak_1$ | 163.2 sec. | 352 sec. |
| $Peak_2$ | — | 381.6 sec. |
| (2) PP9 (perfluoro 1-methyldecalin) | | |
| Attenuation | 8 | 4 |
| Sample | 50 mcl | 100 mcl |
| Peaks | 3 | 7 |
| Retention Time | | |
| $Peak_1$ | 124.8 sec. | 211.2 sec. |
| $Peak_2$ | 136.8 sec. | 240 sec. |
| $Peak_3$ | 196.8 sec. | 340.8 sec. |
| $Peak_4$ | — | 362.4 sec. |
| $Peak_5$ | — | 379.2 sec. |
| $Peak_6$ | — | 391.2 sec. |
| $Peak_7$ | — | 403.2 sec. |
| (3) DAWN (perfluoro 1,3-dimethyladamantane and perfluorotrimethylbicyclo[3.3.1]nonane) | | |
| Attenuation | 8 | 8 |
| Sample | 10 mcl | 100 mcl |
| Peaks | 1 | 5 |
| Retention Time | | |
| $Peak_1$ | 276 sec. | 645.6 sec. |
| $Peak_2$ | — | 705.6 sec. |
| $Peak_3$ | — | 720 sec. |
| $Peak_4$ | — | 729.6 sec. |
| $Peak_5$ | — | 751.2 sec. |

*Antek 300 Gas Chromatography instrument
**Supelco, Inc. Packed Column
***Scientific Glass Engineering Capillary Column
****pl/ml = picoliters/milliliter The above perfluorocarbons all have in common a high solubility in oxygen and carbon dioxide, inertness, transparency, and they are suitable for introduction into the eye in the treatment of ophthalmological disorders, e.g., vitreous replacement. A particular perfluorocarbon or a mixture of perfluorocarbons falling within the family of liquids exemplified by the above derivatives may be used according to the principles of my invention. One main property generic to the preference of the liquids according to this invention over other fluoro-containing liquids is their chemical structure rendering them RES-phobic. These compounds have been defined in my U.S. Pat. No. 3,911,138 as "perfluorocyclocarnane, perfluorinated bicyclooctane, perfluorinated adamantane hydrocarbon, perfluoromethyladamantane and perfluorodimethylbicyclo[3.3.1]nonane, perfluorodimethyladamantane and perfluorotrimethylbicyclo[3.3.1.-]nonane, and perfluorotetrahydrodicyclopentadiene and perfluorobicyclo[5.3.0]decane. RES-phobic perfluorinated liquids tend to accumulate less in the bodies of animals, principally in the liver, and to a lesser extent in the spleen and kidneys. This is significant because such liquids will not become fixed indefinitely within the cells of the organ. There is another property associated with this class of perfluorocarbons that is preferentially utilized when they are introduced into the eye. A perfluorocarbon or a mixture thereof is preferably employed having a vapor pressure within the range of about 1 to about 25 torrs at about 35° C. Thus, such liquids or mixtures are not only RES-phobic, but upon escaping the cell expediently, they will not cause adverse gas collection in the tissue of animals.

In its broadest aspect, the method of my invention involves the introduction of liquid perfluorocarbons into the eye to treat ophthalmological disorders. The liquid can be introduced into the intraocular structure of the eye by different methodologies of injection. For example, the neat liquid can be injected into the aqueous or vitreous by inserting a needle through the pars plana ciliaris and the perfluorocarbon liquid can be introduced slowly. The objective is to introduce neat liquid into the anterior or posterior chamber to form one large volume rather than having it disperse into small droplets (fish-egging). Because the cohesiveness of perfluorocarbon liquids is very high, i.e., the liquids have strong coalescing properties, the fish-egg phenomenon can be avoided. Fish-egging will enhance the turbidity of the substitute, interfering adversely with the visual process. Also, intraocular pressures greater than 30 mm should be avoided to prevent arterial occlusion. It is possible to monitor the intraocular pressure via the Schiotz Tonometer or another needle, or the same one by halting the injection momentarily, and monitoring the pressure within the syringe. The introduction of the liquid into the anterior or posterior chamber is expected to momentarily raise intraocular pressure. The increased intraocular pressure, however, will immediately return to normal due to the dynamic state of the fluids within the eye, i.e., the interaction of the hydrostatic, osmotic and oncotic forces. The liquid may also be introduced into the anterior or posterior chamber as set forth in U.S. Pat. No. 4,141,973, issued Feb. 27, 1979 to Balazs. This procedure permits the withdrawal of the existing liquid with one syringe while introducing the liquid by a second syringe. The withdrawal and injection method, as in the single injection method, is preferably performed slowly. Where the liquid is introduced into the cornea or lens, i.e., a small amount is introduced by means of single or multiple injections.

Vitreous replacement is indicated, as stated herein above, upon liquefaction or opacification, e.g., age, cellular infiltration and hemorrhage. The perfluorocarbon liquids are optimal substitutes for the vitreous. They can be advantageously designed to have similar physical properties of the vitreous being replaced. For example, volume, transparency, consistency, rigidity as well as viscoelasticity, i.e., viscosity and elasticity, can all be incorporated in the preparation of the liquid. Among other advantages, these liquids have similar refractive indices, higher solubilities for oxygen and carbon dioxide, immiscibility with blood and water, cohesiveness and inertness. Because perfluorocarbons generally are immiscible with blood and water, the removal of future cellular infiltration or hemorrhage into the substituted vitreous can be accomplished much easier. More importantly, the disadvantages observed with other present vitreous substitutes can be diminished with the perfluorocarbon liquids. Thus, vision that is partially or totally obscured can be restored with these compounds without experiencing the known disadvantages of the present substitutes. For a comparison of physical properties between the perfluorocarbon liquids and human vitreous, see Tables I and III.

TABLE III

| Characteristics | Human Vitreous | Human Aqueous Humor |
| --- | --- | --- |
| Weight | 3.9 g | — |
| Volume | 3.9 ml | 0.25 ml |
| Water content | 98–99.7% | — |
| pH | 7.5 | — |
| Specific gravity | 1.0053 | x1.0000 |
| Refractive index | 1.3349 | 1.3336 |
| Viscosity (relative to water) | — | 1.025–1.040 |
| Flow rate | — | 2 mcl/min. |
| Osmotic pressure | — | 3–5 mO sm/L |
| Liquid state | hydrogel | liquid |

As developed above, these liquids can be used in eye aqueous replacement as well. The unique feature of cohesiveness permits the perfluorocarbon liquids to remain in the anterior chamber indefinitely. In other words, the immiscibility of these liquids with the aqueous, and their coalescing ability preclude their exit from the anterior chamber. However, the newly produced aqueous can still continuously drain from the anterior chamber. Moreover, these liquids do not interact with the cornea or lens because of their inert characteristics. The refractive indices of these liquids also are very similar to aqueous humor. Thus, such liquids are optimal candidates for aqueous replacement. See Tables I and III to compare the physical characteristics of the human aqueous with the perfluorocarbon liquids.

Opaque areas within the cornea or lens can be treated with these perfluorocarbon liquids. Such liquids can be introduced, as described above, into the opaque areas within the cornea or lens providing a small transparent window therein. Thus, partial or total obstructed vision resulting from opaque areas within the cornea or lens can be improved by the transparentizing effect of these liquids. The perfluorocarbon liquids, therefore, can be ideally employed as transparentizing agents within the cornea or lens because of their unique properties comprising inertness, transparency, and high coalescence.

In retinal detachment, the use of perfluorocarbon liquids as a method of treatment is significant. Because perfluorocarbon liquids are inert and more importantly have a density greater than vitreous, the neat liquid can be introduced into the vitreous while the patient is lying in a dorsal position. The mechanics comprise a dense perfluorocarbon liquid encountering the anterior surface of the detached retina. The dense liquid, by means of gravity, will then compress the detached retina enabling retinal reattachment. The significance of such treatment permits the patient to be treated and recover while lying in a dorsal position when retinal reattachment is indicated.

Substituted perfluorocarbon liquids such as perfluorooctylbromide, can be introduced into the aqueous or vitreous of an animal and be used as a radiopaque agent. That is, such fluid can be used to allow X-rays to be taken of the intraocular tissues.

The invention, its principles and objectives will be further understood in view of the following examples with reference to the drawing which is an anatomical illustration of the eye. The drawing is self-explanatory and illustrates the many components of the eye. The aqueous humor is contained within the anterior chamber, whereas the vitreous is located in the vitreous body. The pars plana ciliary, not illustrated, constitutes the posterior two-thirds of the inner surface of ciliary body and it appears grossly smooth. It should be noted that the pars plana ciliary is the site where the syringe is introduced into the eye to reach the aqueous and vitreous.

The following examples illustrate the use of the perfluorocarbon liquids and substituted derivatives thereof in the eyes of experimental animals.

EXAMPLE 1

A single injection containing perfluorooctylbromide (PFOB), was introduced into the eye of an anesthetized, living cat. The injection, using a small syringe and 26 gauge needle of 0.2 milliliter was made into the anterior chamber of the eye. The injection was performed under direct vision where the neat PFOB liquid could be seen to about half-way fill the interior portion of the anterior chamber. The replaced aqueous humor presumably exited through its normal path into blood. Because PFOB has a specific gravity greater than aqueous humor, the introduced liquid remained in the lower half of the anterior chamber. Thus, the interaction of the PFOB with the lens and cornea was monitored in the lower half of the eye and the upper half observed as a controlled area. The condition of the eye looked good. In addition, because of the radiopaque properties of PFOB, X-rays were taken of the cat's eye which confirmed the presence of PFOB in the lower-half of the cat's anterior chamber without adverse effects. After about one year no adverse effects had been observed.

EXAMPLE 2

A single injection containing DAWN (perfluoro 1,3-dimethyladamantane and perfluorotrimethylbicyclo[3.3.1.]nonane) was introduced into each eye of a rabbit. The injection using a small syringe and 27 gauge needle of 0.1 milliliter was made into the anterior chamber of the left eye and another small syringe and 27 gauge needle of 0.1 milliliter was made into the posterior chamber by way of the pars plana ciliary of the right eye. Media and fundi were normal in both eyes after at least about one year. No opacification occured and normal blood vessels were observed.

EXAMPLE 3

A single injection containing PP9 (perfluoro 1-methyldecalin) was introduced intracorneally into the left eye and intralens in the right eye of a rabbit. The injection using a Hamilton syringe and 30 gauge needle of 8 microliters was made into the cornea of the left eye and another Hamilton syringe and 30 gauge needle of 17 microliters into the lens of the right eye. After about two months, no changes were observed in the structure of the eyes and PP9 was still visible. After about five months, the eyes were still clear.

What is claimed is:

1. A method of treating an intraocular structural disorder of an eye comprising introducing into the intraocular structure under treatment a liquid comprising a liquid perfluorocarbon or substituted derivative thereof in an amount effective to treat said intraocular structural disorder.

2. The method of claim 1 wherein said liquid is introduced into the vitreous of the eye.

3. The method of claim 2 wherein said vitreous is substantially replaced with said liquid.

4. The method of claim 2 wherein the introduction of said liquid into said vitreous and the withdrawal of vitreous from said eye is conducted at the same time.

5. The method of claim 1 wherein said liquid is introduced into the aqueous of the eye.

6. The method of claim 5 wherein said aqueous is substantially replaced with said liquid.

7. The method of claim 1 wherein said liquid is introduced into the cornea.

8. The method of claim 7 wherein said liquid is introduced in a sufficient amount to form a substantially transparent window in said cornea.

9. The method of claim 1 wherein said liquid is introduced into the lens.

10. The method of claim 9 wherein said liquid is introduced in a sufficient amount to form a substantially transparent window in said lens.

11. The method of claim 1 wherein said perfluorocarbon or substituted derivative thereof is in a physical state selected from the group consisting of neat liquid, emulsion, gel, solution and suspension.

12. The method of claim 1 wherein said liquid perfluorocarbon is a perfluorocyclocarbon.

13. The method of claim 12 wherein said perfluorocyclocarbon is selected from the group consisting of perfluoro(methylcyclohexane), perfluoro(1,3-dimethylcyclohexane), perfluoro(decahydronaphthalene), perfluoro(decahydro-1-methylnaphthalene), perfluoro(decahydrodimethylnaphthalene), perfluorodimethyladamantane, perfluorotrimethylbicyclo[3.3.1.]nonane, perfluorotetrahydrodicyclopentadiene, perfluorobicyclo[5.3.0.]decane and perfluorodimethylbicyclo[3.3.1.]nonane, or mixtures thereof.

14. The method of claim 1 wherein said liquid perfluorocarbon is radiopaque.

15. The method of claim 14 wherein said perfluorocarbon is selected from the group consisting of a brominated perfluorocarbon and an iodinated perfluorocarbon.

16. The method of claim 14 wherein said liquid perfluorocarbon is perfluorooctylbromide.

17. A method of repairing a retinal disorder of an eye of an animal comprising introducing into the vitreous of said eye a liquid comprising a liquid perfluorocarbon or substituted derivative thereof, locating said animal in a position to provide means for said liquid to maintain the retina against the choroid of said eye to repair said retina, and maintaining said animal in said position for a time to effect said repair.

18. The method of claim 17 wherein said retinal disorder is either a detached or torn retina.

19. The method of claim 17 wherein said liquid is removed from said vitreous after said repair.

20. The method of claim 1 comprising introducing a radiopaque liquid perfluorocarbon or substituted derivative thereof in an amount effective to detect radiopacity and x-raying said intraocular structural disorder.

21. The method of claim 20 wherein said liquid perfluorocarbon is selected from the group consisting of a brominated perfluorocarbon and an iodinated perfluorocarbon.

22. The method of claim 20 wherein said liquid perfluorocarbon is perfluorooctylbromide.

23. A method of treating an intraocular structural disorder of an eye comprising introducing into the intraocular structure under treatment a substantially transparent liquid perfluorocarbon or substituted derivative thereof in an amount effective to treat said intraocular structural disorder.

24. The method of claim 23 wherein said liquid perfluorocarbon is a perfluorocyclocarbon.

25. The method of claim 24 wherein said perfluorocyclocarbon is selected from the group consisting of perfluoro(methylcyclohexane), perfluoro(1,3-dimethylcyclohexane), perfluoro(decahydronaphthalene), perfluoro(decahydro-1-methylnapthalene), perfluoro(decahydrodimethylnaphthalene), perfluorodimethyladamantane, perfluorotrimethylbicyclo[3.3.1.]nonane, perfluorotetrahydrodicyclopentadiene, perfluorobicyclo[5.3.0.]decane and perfluorodimethylbicyclo[3.3.1.]nonane, or mixtures thereof.

26. A method of treating an intraocular structural disorder of an eye comprising introducing a liquid comprising a liquid perfluorocarbon or substituted derivative thereof into a structure of an eye under treatment selected from the group consisting of anterior chamber, a posterior chamber, cornea, lens and vitreous body in an amount effective to treat said disorder.

27. A method of reparing a clouded cornea of an eye comprising introducing a substantially transparent liquid comprising a liquid perfluorocarbon or substituted derivative thereof into said cornea in an amount effective to provide a substantially transparent window therein.

28. The method of claim 27 wherein said liquid perfluorocarbon is a perfluorocyclocarbon.

29. A method of reparing a clouded lens of an eye comprising introducing a substantially transparent liquid comprising a liquid perfluorocarbon or substituted derivative thereof into said lens in an amount effective to provide a substantially transparent window therein.

30. The method of claim 29 wherein said liquid perfluorocarbon is a perfluorocyclocarbon.

* * * * *